United States Patent [19]

DeWitt

[11] Patent Number: 5,214,486
[45] Date of Patent: May 25, 1993

[54] MONITOR PLATE FOR AUTOMATIC PARTICLE DETECTION SYSTEM

[75] Inventor: James G. DeWitt, Sunnyvale, Calif.

[73] Assignee: Hoya Micro Mask, Inc., Sunnyvale, Calif.

[21] Appl. No.: 807,067

[22] Filed: Dec. 12, 1991

[51] Int. Cl.⁵ .......................... G01J 1/02; G01B 11/00
[52] U.S. Cl. ..................................... 356/243; 356/237; 356/394
[58] Field of Search ............... 356/243, 237, 394, 338; 250/562, 563, 572

[56] References Cited

U.S. PATENT DOCUMENTS

| | | | |
|---|---|---|---|
| 3,963,354 | 6/1976 | Feldman et al. | 250/572 |
| 4,386,850 | 6/1983 | Leahy | 356/237 |
| 4,512,659 | 4/1985 | Galbraith et al. | 356/237 |

OTHER PUBLICATIONS

API-3000 Inspection System Specification, Jun. 1990 QC Optics, Inc.

Laser Users Symposium of Technology, MIE Theory and Diffraction, by Prof. Sergey Broude.

Mask Repair Technologies, by Shigeru Noguchi of Dai Nippon Printing Co., Ltd., Saitama, Japan.

Primary Examiner—Richard A. Rosenberger
Assistant Examiner—Hoa Q. Pham
Attorney, Agent, or Firm—Thomas E. Schatzel

[57] ABSTRACT

The present invention provides a verification plate to verify the accuracy and precision of a mask inspection system in detecting contaminated particles. The verification plate is developed on a substrate having a plurality of predefined glass, i.e., transparent, and chrome, i.e., opaque, patterns. A predetermined number of verification particles each with a predefined size, shape, and location are securely disposed on these glass-chrome patterns. The verification plate is preferably produced having both the glass-chrome patterns and the particles arranged in an orderly manner such that a verification process can be automated under the control of a computer program.

12 Claims, 1 Drawing Sheet

MONITOR PLATE FOR AUTOMATIC PARTICLE DETECTION SYSTEM

BACKGROUND OF THE INVENTION

1. Field of the Invention

This invention relates generally to the inspection of a photo mask to detect contaminated particles, and more particularly, to an apparatus to calibrate the accuracy and precision of an optical mask inspection system.

2. Description of the Prior Art

As the mask and reticle designs continue to evolve in complexity and resolution, the detection of submicron contaminants on a photo mask becomes critically important. Nevertheless, the detection of these particles and the assurance of a consistent performance of high accuracy detection also become increasingly difficult. Due to the increasing integration of semiconductor circuits, submicron geometries with complicated patterns are now produced by high energy electron beams under the control of microprocessor managing the mask imaging process. Meanwhile, the high reliability requirement of the integrated circuits (ICs) demands very stringent quality assurance criteria to produce and use absolute defect-free masks. A single particle in a mask can cause manufacturing defects and render a sequence of very costly and sophisticated IC processes useless. Thus it places great importance to detect and remove any contamination or particle from the mask before the IC manufacturing process begins.

A photomask inspection system is used to perform the tasks of detecting the contaminants, determining where these particles are and measuring their sizes. The inspection is usually conducted on a patterned chrome image with a glass substrate of several hundreds square centimeters and the contaminated particles are of various sizes ranging from micrometers to sub-microns in diameter. Instead of using the high power magnifying microscope for particle detection as was practiced in the traditional manufacturing process, the technique of automatic particle detection by laser scattering is applied. Particle detection by laser scattering method is widely used for detecting particles on wafers, on liquid crystal display (LCD) substrates and on reticle/masks. Laser based systems such as QC Optics API-3000 series, Horiba PD-2000 or PD-3000 and the KLA 301/331 are applied for detection of contamination on a photomask as small as 0.5 microns. For an ideal flat surface, the reflected beam has the same angle as the incident beam relative to the flat surface and both beams lie on the same plane. However, when there are defects or contaminants on the surface, the reflected beam is scattered. By optically collecting the scattered beams and by analyzing them, the defects on a mask can be detected and measured.

The complexity of particle detection by the use of an optical inspection system is compounded by several factors. An accurate determination of the number, location, size and shape of the contaminated particles becomes a very difficult task for the following reasons:

1) The angular distribution of the laser beam scattered by the particles depends on the size and shape of the particles, the optical properties of the particles, and the wavelength and polarization of the incident light. For particles of simple shapes, such as spherical, cubic, or cylindrical shapes, there are rigorous electro-magnetic theory to obtain the analytical predictions. However, since the contaminants on a photo mask are random in shape, it is difficult to determine the sizes of the contaminants from the angular distributions.

2) The total intensity of scattering is dependent on the amount of light intercepted by the contaminants from the incident beam which is in turn determined by the particle size, or more precisely the scattering cross sections, and the intensity of the incident beam at that location. The scattering cross section, and therefore the intensity of scattering, is very sensitive to the incident angle of the inspection beam and the shape of the particle. Again, there is no way to ascertain the shape of a contaminated particle. The computation of the sizes of the detected particles are estimates at best due to this limitation.

3). As the line width of the mask becomes smaller and the pattern of a mask becomes more complex, a higher particle sensitivity is required. However, the higher the particle sensitivity the more difficult it is to differentiate between particles and pattern edges. Some new optical system incorporating polarized laser light and new position of the incident beam and detector and the differential detection methods are tested in an attempt to overcome the difficulty.

To overcome these difficulties and to assure that high quality masks are used in IC manufacture without contamination defects, the accuracy of an optical inspection system is often independently verified before an actual inspection is performed. The underlying concept is to verify the accuracy and repeatability of inspection by operating the inspection system on a flat and smooth surface with predetermined and known defects. The accuracy of the inspection system can then be determined by comparing the inspection results and the known defects previously formed on the verification surface.

The independent verification is now conducted by the use of polystyrene spheres. Polystyrene spheres whose sizes can be accurately controlled are used for testing the system performance. Diluted polystyrene liquid contained in a bottle is spreaded by an air brush onto a monitor plate. A random number of polystyrene spheres with accurately controlled size are spreaded onto the surface of a monitor plate. A particle inspection is then performed on the monitor plate. The accuracy of a mask inspection system is verified by repeated inspection of a testing plate to check the consistency of the results of particle detection between several runs of testings. The detectable particle-size threshold of a mask inspection system is determined by performing the particle detection on monitor plate with smaller and smaller polystyrene spheres until no detection of particles can be obtained from the mask inspection system.

Independent accuracy verification by use of polystyrene testing plate has several limitations.

1) There is no quantitative assurance of the number of polystyrene spheres spreaded on the testing plate. If there are inconsistency between two or more times of particle detection with an optical mask inspection system, there is no systematic method to determine which testing result is more accurate. Even if the number of spheres being detected by the optical inspection system are the same between two or more times of detections, there is still no assurance that such detections are accurate because the number of polystyrene spheres is an unknown at the outset of the tests.

2) The polystyrene spheres are randomly distributed on the surface of a testing plate. If two spheres are distributed very closely together, it may be very difficult for an optical inspection system to detect these as two independent particles because of the resolution limitation. If a polystyrene sphere is distributed very close to the edge or the corner of a pattern, the accuracy of the independent verification is hampered because the optical diffraction pattern from the edge or the corner. The diffraction patterns from the edge or corner of a pattern may often obscure the reflecting beam from the polystyrene spheres and make the determination of the location and number of particles on the monitor plate quite complicated.

3) The polystyrene spheres spreaded on the test plate are not securely disposed on the surface. Only a very weak electro-static force binds those spheres to the testing plate surface. Random motions of these polystyrene spheres may occur which may change the detection results between repeated particle detection by a mask inspection system. Repeated use of a polystyrene testing plate is therefore not reliable unless the plate is handled very carefully to assure no random motion of the polystyrene spheres has occurred between tests. Storage of a polystyrene testing plate for later use is extremely difficult because of this limitation and also because the testing plate cannot be cleaned or decontaminated before a later use to assure the quality of testing.

The state-of-the-art optical mask inspection system is therefore limited by these difficulties. Due to these limitations, the accuracy of an optical mask inspection system cannot be independently verified with assurance of ascertainable accuracy. Because of the critical importance in assuring defect-free photo masks in manufacturing the integrated circuits, there is still a great need to overcome these aforementioned limitations.

SUMMARY OF THE PRESENT INVENTION

It is therefore an object of the present invention to provide a mask inspection verification system with precisely disposed particles with predetermined locations, shapes and sizes whereby the performance of a particle detection system of the photo mask can be accurately ascertained.

It is another object of the present invention to provide an accurate, reliable and durable mask inspection verification system which can be repeatedly operated without random variations or degradations of verification performance.

It is a further object of the present invention to provide a method to produce an accurate, reliable and durable mask inspection verification apparatus utilizing modern electronic technology whereby the particles on the verification plates can be accurately produced under the control of a computer to have sub-micron precision.

It is a further object of the present invention to provide a method to produce an accurate, reliable and durable mask inspection verification apparatus whereby the cost and production cycle of production of the integrated circuits (ICs) can be reduced due the more efficient and more accurate mask inspection which in turn leads to improvement in quality control of the photo masks used in IC production.

Briefly, in a preferred embodiment, the present invention comprises of a verification plate having predefined glass, i.e., transparent, and chrome, i.e., opaque, patterns. A predetermined number of verification particles each with a predefined size, shape, and location are securely disposed on these glass-chrome patterns. The verification plate is preferably produced having both the glass-chrome patterns and the particles arranged in an orderly manner such that a verification process can be automated under the control of a computer program.

It is an advantage of the present invention that modern electronic IC manufacturing technology is used to produce the particles on the verification plate whereby the number, sizes, shapes, and locations of the particles are precisely placed on the plate with very small tolerance of inaccuracy which can be as low as in the range of nanometers.

It is another advantage of the present invention that the performance of a mask inspection system can be definitively verified because the number, location, shape and size of all particles disposed on a verification plate are predefined and precisely produced on the plate.

It is a further advantage that a consistent accuracy of verification can be maintained in repeated verification operations because the particles on the verification plate are securely and permanently produced on the plate thus prevent random motion and redistribution of the particles used for verification.

It is a further advantage of the present invention that the cost and production cycle of IC manufacturing are reduced because by providing an accurate, reliable and durable mask inspection verification apparatus, more efficient and more accurate mask inspection can be performed which in turn leads to improvement in quality control of the photo masks used in IC production.

These and other objects and the advantages of the present invention will no doubt become obvious to those of ordinary skill in the art after having read the following detailed description of the preferred embodiment which is illustrated in the various drawing figures.

DETAILED DESCRIPTION OF THE PREFERRED EMBODIMENT

Figure 1:
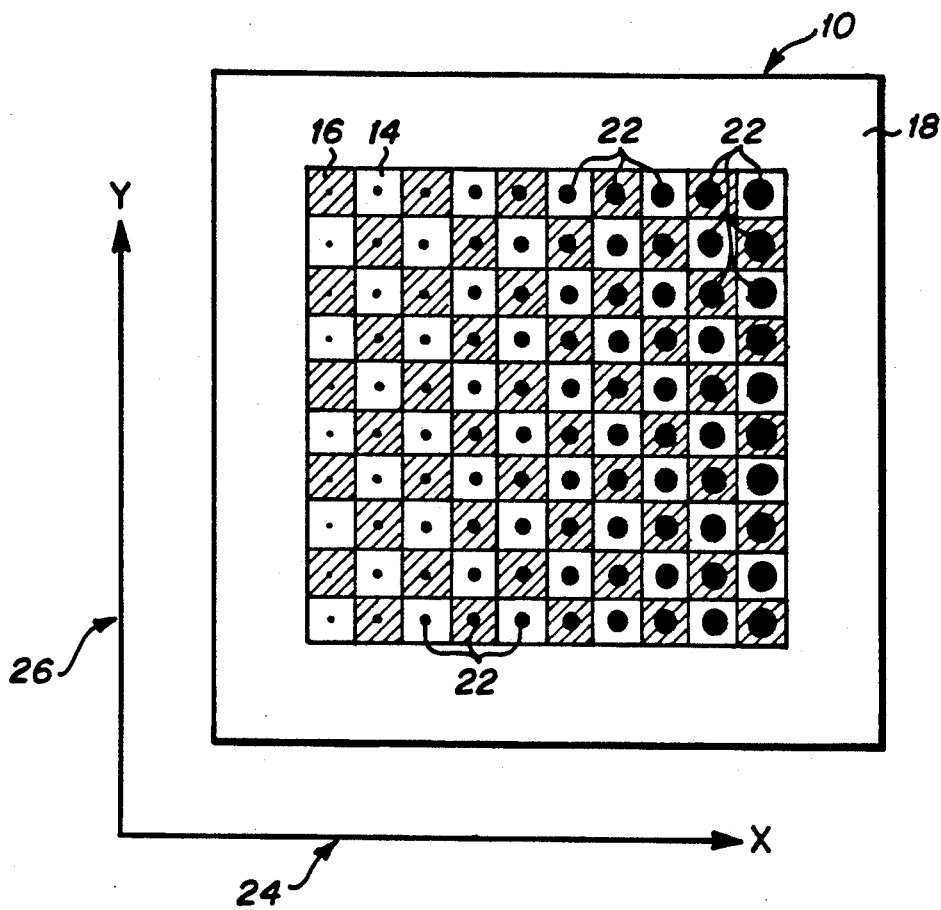
FIG. 1 is a top view of a verification plate according to the present invention.

A verification plate 10 of the present invention is shown in FIG. 1. In this preferred embodiment, a checkerboard pattern of glass squares 14 and chrome squares 16 are formed on substrate 18. These checkerboard square patterns are formed on substrate 18 by the use of typical lithographical processes which is well known by those skilled in the art. Glass squares 14 and chrome squares 16 are arranged into rows and columns wherein an alternating patterns between glass and chrome squares are formed. A verification particle 22 is deposited at the center of each glass square 14 and chrome square 16.

With the advent of modern electronic technology, there are several techniques to form a predetermined number of verification particles 22 with precise shape, size, and locations on substrate 18. These particles can be created by first depositing a plurality of layers of thin films on a substrate. Different layers of thin film can then be etched or lift-off methods can be applied to remove these thin film layers except where the verification particles are predefined to be deposited. Alternatively, selective exposure on a resisted photo mask and sputtering techniques can be applied to form verification particles at predefined locations having predetermined sizes and shapes.

Figure 2:
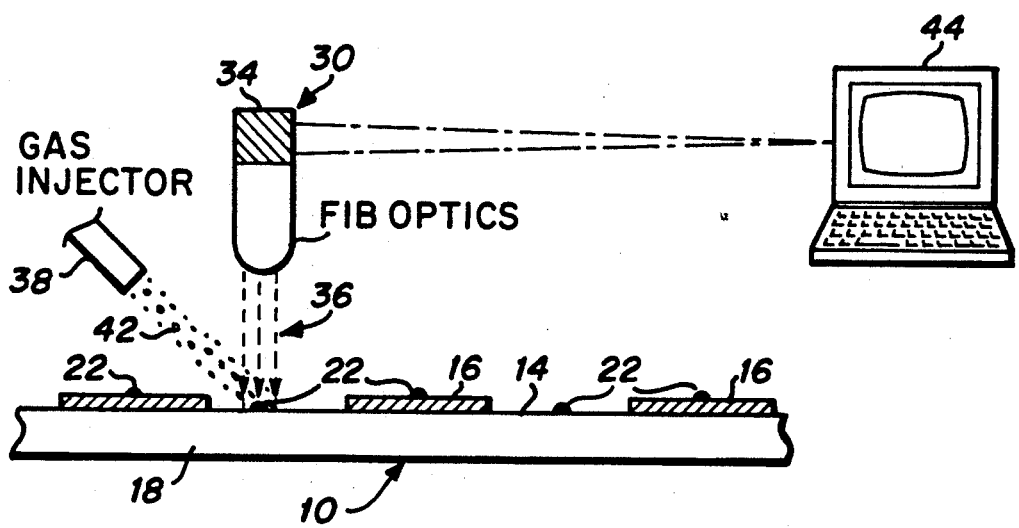
FIG. 2 is a schematic diagram showing a focus ion beam system deposits a plurality of verification particles onto a verification plate.

A schematic illustration of a focused ion beam (FIB) system 30 for forming verification particles 22 on substrate 18 is shown in FIG. 2. Focus ion beam (FIB) system 30 with an ion source 34 injects an ion beam 36 onto verification plate 10. A gas injector 38 injects gas molecules 42 onto the surface of verification plate 10. Verification particles 22 are formed on top of chrome and glass patterns 14 and 16. FIB system 30 is under the control of a computer 44. An user can control the FIB system 30 to form verification particles 22 at a predetermined locations in either a chrome or a glass pattern 14 and 16 with predetermined size, shape and height.

By the use of FIB system 30, a plurality of verification particles 22 are deposited. Referring to FIG. 1 where X-axis 24 pointing from left to right and Y-axis 26 pointing from bottom to top are shown. For each column, the X-Y dimensions of the verification particles 22 are arranged to be the same. While the heights of particles 22 are the same for all the squares 14 and 16 of each row. Meanwhile, the X-Y dimensions of verification particles 22 of one column is sequentially increased from one column to the next as one moves from the left to the right across the verification plate 10 and the heights of verification particles are decreased from the top row sequentially as one moves from the top to the bottom. In one example of the preferred embodiments, substrate 18 is 5 inches by 5 inches and each square pattern 14 and 16 has a dimension of 5 mm by 5 mm. Verification particles 22 have X-Y dimensions increase from 0.3 micron by 0.3 micron to 1.0 microns by 1.0 microns along the X-axis and the height is increased from 0.2 micron to 1.0 microns along the Y axis.

Verification particles 22 are permanently and securely formed on verification plate 10 with predetermined sizes and shapes at precisely controlled locations. With proper care, verification plate can be stored and cleaned for repeated use. By arranging verification particles in rows and columns and by gradually and sequentially increasing or decreasing the sizes of verification particles 22 in an orderly manner, the particle detection accuracy of a mask optical inspection system can by systematically verified. Additionally, the size-detection threshold of an inspection system can be easily determined by comparing the results of particle inspection with the predetermined sizes and distributions of verification particles 22. The performance of a mask inspection system can therefore be definitively verified.

Since an optical inspection system can be verified by one verification plate repetitively over the life of the inspection system, a historic verification data can be accumulated and a statistical analysis can be preformed on the accumulated verification results to statistically determine the precision of the optical inspection system. The more the accumulated historic data, the more likely the precision of the optical inspection system can be statistically quantified with higher confidence level.

In addition to the verification operations as described above, a verification plate according to the present invention can also be applied for the determination of parametric sensitivities of an optical inspection system. Parametric variations such as shapes, sizes, proximity of adjacent particles, particles having a variety of material characteristics, etc., can be made by depositing verification particles 22 under the control of an FIB controlling computer or other particle deposition techniques commonly available in the electronic industry. Performance sensitivities of an optical inspection system can be investigated by conducting a particle inspection on the verification plates having verification particles 22 comprising such parametric variations. Improvements to optical inspection systems can be achieved by increasing the accuracy and reliability of the inspection system based on the results of these sensitivity studies.

Although the present invention has been described in terms of the presently preferred embodiment, it is to be understood that such disclosure is not to be interpreted as limiting. Various alternations and modifications will no doubt become apparent to those skilled in the art after reading the above disclosure. Accordingly, it is intended that the appended claims be interpreted as covering all alternations and modifications as fall within the true spirit and scope of the invention.

I claim:

1. A verification plate to verify the accuracy of a mask inspection system in detecting contaminated particles comprising:
   a substrate having a plurality of glass patterns and a plurality of chrome patterns formed thereon; and
   a predetermined number of verification particles each having a predetermined shape and size, each of the verification particle being deposited on top of said glass and chrome patterns at a predetermined location whereby the accuracy of said mask inspection system can be definitely verified by performing an inspection operation on the verification plate.

2. A verification plate of claim 1 wherein:
   said glass and chrome patterns are square patterns on the substrate.

3. A verification plate of claim 2 wherein:
   said plurality of verification particles are deposited on top of said glass and chrome pattern in such manner that each of said square glass or chrome patterns has one verification particle deposited thereon.

4. A verification plate to verify the accuracy of a mask inspection system in detecting contaminated particles comprises:
   a substrate having a plurality of square glass patterns and a plurality of square chrome patterns formed thereon each of said square glass patterns and each said square chrome patterns is of equal dimensions, said square glass and chrome patterns are further arranged in a plurality of rows and columns wherein each row and each column are arranged to have one of said glass pattern adjacent to one of said square chrome pattern whereby a checkerboard pattern having an alternating glass and chrome pattern is formed on the substrate;
   a predetermined number of verification particles each having a predetermined shape and each particle is deposited at the center of one of said square glass and chrome patterns, said plurality of verification particles are further arranged such that each column of said glass and chrome patterns having particles of one predetermined size, and further that said particle size for one of said columns is sequentially increased from one column to an adjacent column across the surface of the verification plate whereby the accuracy and a size detection threshold of the mask inspection system can be effectively and accurately verified.

5. A verification plate as set forth in claim 4 wherein:

said verification particles are further being arranged such that said verification particles in each of said row of squares having a same predetermined height while the height of said verification particles for one row of said squares is sequentially decreased from one of said rows to an adjacent row across the surface of the verification plate whereby the accuracy and height detection threshold of the mask inspection system can be effectively and accurately verified.

6. A method to verify the accuracy of a mask inspection system in detecting contaminated particles comprising the steps of:
(a) making a verification plate wherein said verification plate comprises:
a substrate having a plurality of glass patterns, and a plurality of chrome patterns found thereon; and
a predetermined number of verification particles each having a predetermined shape and size, each of the verification particles being deposited on top of said glass and chrome patterns at a predetermined location;
(b) performing a mask inspection of said verification plate to obtain a measurement of the number, size, location and shape of all of said verification particles on said verification plate; and
(c) comparing said measurement obtained from step (b) to said predetermined number, size, shape and location of said verification particles deposited on the verification plate as defined in step (a) whereby the accuracy of said mask inspection system can be definitely verified.

7. A method to quantify the precision of a mask inspection system in detecting contaminated particles comprising the steps of:
(a) making a verification plate wherein said verification plate comprises;
a substrate having a plurality of glass patterns and a plurality of chrome patterns formed thereon; and
a predetermined number of verification particles each having a predetermined shape and size, each of the verification particles being deposited on top of said glass and chrome patterns at a predetermined location;
(b) performing a mask inspection on said verification plate repetitively to obtain a plurality of measurements of the number, size, location and shape of all of said verification particles on said verification plate; and
(c) performing a statistical analysis on said measurements obtained from step (b) and comparing results obtained from said analysis to said predetermined number, size, shape and location of said verification particles deposited on the verification plate as defined in step (a) whereby the precision of said mask inspection system can be definitively quantified.

8. A method to make a verification plate to verify the accuracy of a mask inspection system in detecting contaminated particles comprises:
(a) generating a plurality of glass patterns and a plurality of chrome patterns on a substrate; and
(b) depositing a predetermined number of verification particles each having a predetermined shape and size, each of the verification particles being securely deposited on top of said glass and said chrome patterns at a predetermined location.

9. A method to make verification plate of claim 8 wherein step (b) further comprises a step of:
(b1) depositing said verification particles by using a focus ion beam (FIB) induced deposition whereby said predetermined number of verification particles can be precisely deposited at said predetermined locations having said predetermined shapes and sizes.

10. An integrated circuit (IC) manufactured by use of a photomask wherein a method is used to verify the accuracy of a mask inspection system in detecting contaminated particles on said photomask comprising the steps of:
(a) making a verification plate wherein said verification plate comprises:
a substrate having a plurality of glass patterns and a plurality of chrome patterns formed thereon; and
a predetermined number of verification particles each having a predetermined shape and size, each of the verification particles being securely deposited on top of said glass and chrome patterns at a predetermined location;
(b) performing a mask inspection on said verification plate to obtain a measurement of the number, size, location and shape of all of said verification particles on said verification plate; and
(c) comparing said measurement obtained from step (b) to said predetermined number, size, shape and location of said verification particles deposited on the verification plate as defined in step (a) whereby the accuracy of said mask inspection system can be definitively verified.

11. An electronic apparatus including at least one integrated circuit (IC) manufactured by use of a photomask wherein a method is used to verify the accuracy of a mask inspection system in detecting contaminated particles on said photomask comprising the steps of:
(a) making a verification plate wherein said verification plate comprises:
a substrate having a plurality of glass patterns and plurality of chrome patterns formed thereon; and
a predetermined number of verification particles each having a predetermined shape and size, each of the verification particles being securely deposited on top of said glass and chrome patterns at a predetermined location;
(b) performing a mask inspection on said verification plate to obtain a measurement of the number, size, location and shape of all of said verification particles on said verification plate; and
(c) comparing said measurement obtained from step (b) to said predetermined number, size, shape and location of said verification particles deposited on the verification plate as defined in step (a) whereby the accuracy of said mask inspection system can be definitively verified.

12. A data handling apparatus including at least one integrated circuit (IC) manufactured by use of a photomask wherein a method is used to verify the accuracy of a mask inspection system in detecting contaminated particles on said photomask comprising the steps of:
(a) making a verification plate wherein said verification plate comprises:
a substrate having a plurality of glass patterns and a plurality of chrome patterns formed thereon; and
a predetermined number of verification particles each having a predetermined shape and size, each of the verification particles being securely deposited on top of said glass and chrome patterns at a predetermined location;

(b) performing a mask inspection on said verification plate to obtain a measurement of the number, size, location and shape of all of said verification particles on said verification plate; and (c) comparing said measurement obtained from step (b) to said predetermined number, size, shape and location of said verification particles deposited on the verification plate as defined in step (a) whereby the accuracy of said mask inspection system can be definitively verified.

* * * * *